US006461812B2

(12) United States Patent
Barth et al.

(10) Patent No.: US 6,461,812 B2
(45) **Date of Patent: *Oct. 8, 2002**

(54) METHOD AND MULTIPLE RESERVOIR APPARATUS FOR FABRICATION OF BIOMOLECULAR ARRAYS

(75) Inventors: Phillip W. Barth, Portola Valley; Michael P. Caren, Palo Alto; William H. McAllister, Saratoga; Carol T. Schembri, San Mateo; Arthur Schleifer, Portola Valley, all of CA (US)

(73) Assignee: Agilent Technologies, Inc., Palo Alto, CA (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/150,507

(22) Filed: Sep. 9, 1998

(65) Prior Publication Data

US 2001/0051334 A1 Dec. 13, 2001

(51) Int. Cl.[7] .......................... C12Q 1/68; C12M 1/36; G01N 15/06; B01L 3/02; B41J 0/35

(52) U.S. Cl. .................... 435/6; 435/283.1; 435/286.2; 435/288.2; 435/287.2; 435/288.5; 422/55; 422/56; 422/58; 422/61; 422/68.1; 422/100; 347/20; 436/5

(58) Field of Search .......................... 422/100, 55, 56, 422/58, 64, 68.1; 435/6, 283.1, 286.2, 287.2, 288.2, 288.5; 347/20; 436/518

(56) References Cited

U.S. PATENT DOCUMENTS 4,115,200 A 9/1978 Anderson .................. 195/127
4,184,169 A 1/1980 Taylor et al. ............ 46/140 R (List continued on next page.)

FOREIGN PATENT DOCUMENTS

EP 514948 A1 11/1992 .......... G01N/35/06
EP 0742287 A2 11/1996 .............. C12Q/1/6

(List continued on next page.)

OTHER PUBLICATIONS

Khrapko, K.R. et al., "A Method for DNA Sequencing by Hybridization with Oligonucleotide Matrix", *DNA Sequence—J. DNA Sequencing and Mapping,* 1991, vol. 1, pp. 375–388.

(List continued on next page.)

*Primary Examiner*—W. Gary Jones
*Assistant Examiner*—B J Forman
(74) *Attorney, Agent, or Firm*—Gordon M. Stewart

(57) ABSTRACT

Apparatus for delivering a plurality of different biological materials onto discrete locations on a receiving surface, as for example to fabricate an array of different biological material, includes a plurality of orifices in an orifice member, at least six delivery chambers each in fluid conducting relationship with at least one of the orifices, a plurality of reservoirs each in fluid communication with at least one of the delivery chambers, means associated with each orifice for propelling fluid through the associated orifice from the delivery chamber that is in fluid conducting relationship with the orifice, and a vent for commonly venting at least two of the reservoirs. In some embodiments the chambers and reservoirs are loaded with fluids containing selected biomolecules by drawing the selected fluids into the chambers through the orifices; in other embodiments the fluids are introduced into the reservoirs. Also, methods for depositing biological materials onto a surface, as for example to fabricate a biomolecular array, employ the apparatus.

58 Claims, 7 Drawing Sheets

U.S. PATENT DOCUMENTS

| | | | | | |
|---|---|---|---|---|---|
| 4,477,578 | A | | 10/1984 | Miles et al. | 436/518 |
| 5,003,059 | A | | 3/1991 | Brennan | 536/27 |
| 5,174,962 | A | | 12/1992 | Brennan | 422/78 |
| 5,180,606 | A | | 1/1993 | Stokes et al. | 427/2 |
| 5,326,691 | A | | 7/1994 | Hozier | 435/6 |
| 5,378,638 | A | | 1/1995 | Deeg et al. | 436/518 |
| 5,382,511 | A | | 1/1995 | Stapleton | 435/6 |
| 5,442,384 | A | * | 8/1995 | Schantz et al. | 347/20 |
| 5,466,575 | A | | 11/1995 | Cozzette et al. | 435/6 |
| 5,474,796 | A | | 12/1995 | Brennan | 427/2.13 |
| 5,477,255 | A | | 12/1995 | Huth | 347/87 |
| 5,501,984 | A | | 3/1996 | Hofstetter et al. | 436/518 |
| 5,510,817 | A | | 4/1996 | Sohn | 347/21 |
| 5,527,681 | A | | 6/1996 | Holmes | 435/6 |
| 5,529,756 | A | | 6/1996 | Brennan | 422/131 |
| 5,539,952 | A | | 7/1996 | Hayes et al. | 15/321 |
| 5,541,057 | A | | 7/1996 | Bogart et al. | 435/5 |
| 5,545,531 | A | | 8/1996 | Rava et al. | 435/6 |
| 5,550,063 | A | | 8/1996 | Bogart | 436/518 |
| 5,552,272 | A | | 9/1996 | Bogart | 435/6 |
| 5,554,339 | A | | 9/1996 | Cozzette et al. | 422/50 |
| 5,554,501 | A | | 9/1996 | Coassin et al. | 435/6 |
| 5,556,752 | A | | 9/1996 | Lockhart et al. | 435/6 |
| 5,561,071 | A | | 10/1996 | Hollenberg et al. | 437/1 |
| 5,563,060 | A | | 10/1996 | Hozier | 435/240.23 |
| 5,563,639 | A | | 10/1996 | Cameron et al. | 347/34 |
| 5,595,785 | A | | 1/1997 | Hindagolla et al. | 427/271 |
| 5,599,695 | A | | 2/1997 | Pease et al. | 435/91.1 |
| 5,609,908 | A | | 3/1997 | Voss | 427/214 |
| 5,610,287 | A | | 3/1997 | Nikiforov et al. | 536/24.3 |
| 5,618,671 | A | | 4/1997 | Lindstrom | 435/6 |
| 5,620,894 | A | | 4/1997 | Barger et al. | 435/286.2 |
| 5,624,711 | A | | 4/1997 | Sundberg et al. | 427/261 |
| 5,624,815 | A | | 4/1997 | Grant et al. | 435/30 |
| 5,631,171 | A | | 5/1997 | Sandstrom et al. | 436/518 |
| 5,635,966 | A | | 6/1997 | Keefe et al. | 347/43 |
| 5,635,968 | A | | 6/1997 | Bhaskar et al. | 347/59 |
| 5,636,441 | A | | 6/1997 | Meyer et al. | 29/890.1 |
| 5,639,603 | A | | 6/1997 | Dower et al. | 435/6 |
| 5,639,671 | A | | 6/1997 | Bogart et al. | 436/518 |
| 5,642,142 | A | | 6/1997 | Bohorquez | 347/15 |
| 5,646,039 | A | | 7/1997 | Northrup et al. | 435/287.2 |
| 5,658,728 | A | | 8/1997 | Gosney, Jr. | 435/6 |
| 5,658,734 | A | | 8/1997 | Brock et al. | 435/6 |
| 5,658,802 | A | | 8/1997 | Hayes et al. | 436/518 |
| 5,665,566 | A | | 9/1997 | LaVallie | 435/69.3 |
| 5,677,195 | A | | 10/1997 | Winkler et al. | 436/518 |
| 5,677,577 | A | | 10/1997 | Barbehenn et al. | 307/98 |
| 5,679,524 | A | | 10/1997 | Nikiforov et al. | 435/6 |
| 5,679,773 | A | | 10/1997 | Holmes | 530/334 |
| 5,682,188 | A | | 10/1997 | Meyer et al. | 347/61 |
| 5,683,881 | A | | 11/1997 | Skiena | 435/6 |
| 5,700,637 | A | | 12/1997 | Southern | 435/6 |
| 5,714,989 | A | | 2/1998 | Wade | 347/14 |
| 5,726,690 | A | | 3/1998 | Bohorquez et al. | 347/15 |
| 5,733,509 | A | | 3/1998 | Ackley et al. | 422/131 |
| 5,736,188 | A | | 4/1998 | Alcock et al. | 427/2.11 |
| 5,736,995 | A | | 4/1998 | Bohorquez et al. | 347/14 |
| 5,736,998 | A | | 4/1998 | Caren et al. | 347/45 |
| 5,745,128 | A | | 4/1998 | Lam et al. | 346/140.1 |
| 5,772,829 | A | | 6/1998 | Cowger | 156/291 |
| 6,001,309 | A | * | 12/1999 | Gamble et al. | 422/100 |
| 6,028,198 | A | * | 2/2000 | Blanchard | 536/23.1 |
| 6,083,763 | A | * | 7/2000 | Balch | 436/518 |
| 6,188,416 | B1 | * | 2/2001 | Hayes | 347/71 |

FOREIGN PATENT DOCUMENTS

| | | | |
|---|---|---|---|
| EP | 0799897 A1 | 10/1997 | C12Q/1/68 |
| EP | 0705699 B1 | 6/1998 | B41J/2/165 |
| WO | WO 89/10977 | 11/1989 | C12Q/1/68 |
| WO | WO 93/17126 | 9/1993 | C12Q/1/68 |
| WO | WO 93/23552 | 11/1993 | C12N/15/87 |
| WO | WO 95/11995 | 5/1995 | C12Q/1/68 |
| WO | WO 95/35505 | 12/1995 | G01N/33/543 |

OTHER PUBLICATIONS

D.B. Wallace et al., "Multi–fluid Ink–Jet Array for Manufacturing of Chip–Based Microarray Systems", Proceedings, Second International Conference on Microreaction Technology, New Orleans, Mar., 1998 (alleged), 5pp. (as downloaded from www.microfab.com on Feb. 26, 2001) (color copy).

D.B. Wallace et al., "Ink–Jet Microdispensing for Biomedical Applications", Cambridge Healhtech Conference on Microfabrication Technology, San Jose, Nov. 1997 (alleged), 26pp. (as downloaded from www.microfab.com on Feb. 26, 2001) (color copy).

Trost, Hans–Jochen et al., "Ink Jet Technology for Biomedical Applications", 16th Annual Houston Conference on Biomedical Engineering Research, Apr. 1998 (alleged), pp. 1–8, 12, and 14–28 . (as downloaded from www.microfab-.com on Feb. 26, 2001) (color copy).

Fodor et al., "Light–Directed, Spatially Addressable Parallel Chemical Synthesis", *Science,* 1991, vol. 251, pp. 767–773.

Lockhart et al., "Expression Monitoring by Hybridization to High–Density Oligonucleotide Arrays", *Nature Biotechnology,* 1996, vol. 14, pp. 1675–1680.

Schena et al., "Quantitative Monitoring of Gene Expression Patterns with a Complementary DNA Microarray", *Science,* vol. 270, pp. 467–470.

Schena et al., "Parallel Human Genome Analysis: Microarray–based Expression Monitoring of 1000 Genes", *Proc. Natl. Acad. Sci. USA,* 1996, vol. 93, pp. 10614–10619.

Shalon et al., "A DNA Microarray System for Analyzing Complex DNA Samples Using Two–color Fluorescent Probe Hybridization", *Genome Research,* 1996, vol. 6, pp. 639–645.

Milosavljevic et al., "Discovering Distinct Genes Represented in 29,570 Clones from Infant Brain cDNA Libraries by Applying Sequencing by Hybridization Methodology", *Genome Research,* 1996, vol. 6, pp. 132–141.

Nguyen et al., "Differential Gene Expression in the Murine Thymus Assayed by Quantitative Hybridization of Arrayed cDNA Clones", *Genomics,* 1995, vol. 29, pp. 207–216.

Pietu et al., "Novel Gene Transcripts Preferentially Expressed in Human Muscles Revealed by Quantitative Hybridization of a High Density cDNA Array", *Genome Research,* 1996, vol. 6, pp. 492–503.

Zhao et al., "High–density cDNA Filter Analysis: A Novel Approach for Large–scale, Quantitative Analysis of Gene Expression", *Gene,* vol. 156, pp. 207–213.

Chalifour et al., "A Method for Analysis of Gene Expression Patterns", *Analytical Biochemistry,* 1994, vol. 216, pp. 299–304.

Heller et al., "Discovery and Analysis of Inflammatory Disease–related Genes Using cDNA Microarrays", *Proc. Natl. Acad. Sci. USA,* 1997, vol. 94, pp. 2150–2155.

Lehrach et al., "Hybridization Fingerprinting in Genome Mapping and Sequencing", *Genome Analysis* vol. 1: *Genetic and Physical Mapping,* 1990, (Davies & Tilgham, Eds.) Cold Spring Harbor Laboratory Press, pp. 39–81.

Schema, "Genome Analysis with Gene Expression Microarrays", *BioEssays,* 1996, vol. 18, No. 5, pp. 427–431.

* cited by examiner

METHOD AND MULTIPLE RESERVOIR APPARATUS FOR FABRICATION OF BIOMOLECULAR ARRAYS

RELATED APPLICATIONS

This application is related to U.S. application Ser. No. 09/150,504, filed on the same date as this application, titled "Method and Apparatus for Making Nucleic Acid Arrays", hereby incorporated herein by reference in its entirety.

BACKGROUND

This invention relates to biomolecular arrays and, particularly, to methods and apparatus for depositing biological materials in a pattern of array features on a surface of a solid support.

Arrays of binding agents have become an increasingly important tool in the biotechnology industry and related fields. Such arrays, in which such binding agents as oligonucleotides or peptides are deposited onto a solid support surface in the form of an array or pattern, can be useful in a variety of applications, including gene expression analysis, drug screening, nucleic acid sequencing, mutation analysis, and the like.

Such arrays may be prepared in any of a variety of different ways. For example, DNA arrays may be prepared manually by spotting DNA onto the surface of a substrate with a micro pipette. See, Khrapko et al. (1991), DNA Sequence 1:375–388. Or, a dot-blot approach or a slot-blot approach may be employed in which a vacuum manifold transfers aqueous DNA samples from a plurality of wells to a substrate surface. Or, an array of pins can be dipped into an array of fluid samples and then contacted with the substrate surface to produce the array of sample materials. Or, an array of capillaries can be used to produce biopolymeric arrays, as described for example in International Patent Publication WO 95/35505.

In an alternative approach, arrays of biopolymeric agents are constructed in discrete regions on the surface of the substrate. See, e.g., U.S. Pat. No. 5,143,854; and Fodor, et al. (1991), Science 251:767–773.

There is a continued interest in developing methods and devices for making arrays of biomolecules, in which the apparatus is less complicated and more automated and the methods reduce waste of biological material that may be in limited supply, and which result in efficient and reproducible rapid production of more versatile and reliable arrays.

Arrays of biomolecular materials, and methods for their fabrication, are described for example in U.S. Pat. Nos.: 5,242,974; 5,384,261; 5,405,783; 5,412,087; 5,424,186; 5,429,807; 5,436,327; 5,445,934; 5,472,672; 5,527,681; 5,529,756; 5,545,531; 5,554,501; 5,556,752; 5,561,071; 5,599,695; 5,624,711; 5,639,603; and 5,658,734; in International Patent Publications WO 93/17126; WO 95/11995; and WO 95/35505; and in European Patent Publications EP 742 287; and EP 799 897.

Other publications of interest include: Lockhart, et al. (1996), Nature Biotechnology 14: 1675–1680; Schena, et al. (1995), Science 270: 467–470; Schena, et al. (1996), Proc. Nat'l. Acad. Sci. USA 93:10614–10619; Shalon, et al. (1996), Genome Res. 6: 639–645; Milosavljevic, et al. (1996), Genome Res. 6:132–141; Nguyen, et al. (1995), Genomics 29: 207–216; Piétu, et al. (1996), Genome Res. 6: 492–503; Zhao, et al. (1995), Gene 166:207–213; Chalifour, et al. (1994), Anal. Biochem. 216:299–304; Heller, et al. (1997), Proc. Nat'l Acad. Sci. USA 94: 2150–2155; Lehrach, et al. (1990), Hybridization Fingerprinting in Genome Mapping and Sequencing, Genome Analysis, Vol. 1 (Davies & Tilgham, eds.) (Cold Spring Harbor Press) pp. 39–81; and Schema (1996), BioAssays 18: 427–431.

The use of inkjet printing devices to dispense biochemical agents such as proteins and nucleic acids is suggested or disclosed in, for example, U.S. Pat. Nos. 5,658,802; 5,338,688; 5,700,637; 5,474,796; 4,877,745; and 5,449,754.

SUMMARY OF THE INVENTION

In one general aspect the invention features apparatus for delivering a plurality of different biological materials onto discrete locations on a receiving surface, the apparatus including a plurality of orifices in an orifice member, at least six delivery chambers each in fluid conducting relationship with at least one of the orifices, a plurality of reservoirs each in fluid communication with at least one of the delivery chambers, and means associated with each orifice for propelling fluid through the associated orifice from the delivery chamber that is in fluid conducting relationship with the orifice.

In another general aspect the invention features apparatus for delivering a plurality of different biological materials onto discrete locations on a receiving surface, the apparatus including a plurality of orifices in an orifice member, at least six delivery chambers each in fluid conducting relationship with at least one of the orifices, a plurality of reservoirs each in fluid communication with at least one of the delivery chambers, means associated with each orifice for propelling fluid through the associated orifice from the delivery chamber that is in fluid conducting relationship with the orifice, and a vent for commonly venting at least two of the reservoirs.

In some embodiments the propelling means propels the fluid through the associated orifice by forming a bubble that displaces the fluid; particular bubble-forming means include a source of heat such as an electrical resistor. In other embodiments the propelling means propels the fluid through the associated orifice by electromechanical displacement; particular electromechanical displacement means include a piezoelectric device.

In some embodiments the orifice member is a generally planar orifice plate, and the orifices provide openings through from an inner surface to an exit surface of the plate; the apparatus further includes a back member having a generally planar surface facing the inner surface of the orifice plate; and the inner surface of the orifice plate and the facing surface of the back member are spaced apart by a barrier. The barrier is configured so that the barrier, the inner surface of the orifice plate, and the facing surface of the back member define the delivery chambers. In some such embodiments the fluid propelling means are situated on or in the back member, or on or in the barrier. Usually, the back member is constructed as a silicon die, and the fluid propelling means are formed within the silicon die by techniques that are conventional to solid state electronic device construction.

In another general embodiment the invention features apparatus for depositing a plurality of different biological materials onto discrete locations on a receiving surface, the apparatus including an orifice plate defining a plurality of orifices; a substrate connected to the orifice plate and defining a plurality of delivery chambers and a plurality of reservoirs, each of the orifices being in fluid communication with a reservoir by way of a delivery chamber; means adjacent each orifice for propelling fluid through the orifice from the delivery chamber that provides fluid communication with the orifice and reservoir; and common means for generating a pressure differential within at least a plurality of the delivery chambers.

In some embodiments each delivery chamber is connected to a fluid reservoir by way of a conduit. Accordingly, in another general aspect the invention features apparatus for depositing a plurality of different biological materials onto discrete locations on a receiving surface, the apparatus comprising an orifice member defining a plurality of orifices therethrough from a first surface to a second surface thereof; a barrier affixed to the first surface of the orifice member, the barrier and the orifice member together defining a plurality of delivery chambers each of which is in fluid communication with one of the orifices, and the barrier and the orifice member together defining a plurality of fluid reservoirs; the orifice member further having a plurality of channels, each of which has an opening in the first surface to one of the delivery chambers and an opening in the first surface to one of the reservoirs, and each of which provides fluid communication between the delivery chamber and the fluid reservoir to which it opens; and means associated with each orifice for propelling fluid through the orifice from the delivery chamber that is in fluid communication with the orifice.

The apparatus according to the invention is usefull in methods for delivering biological materials in a patterned array on a solid surface.

Accordingly, in another general aspect the invention features a method for delivering a plurality of different biological materials onto discrete locations on a receiving surface, the method comprising loading a fluid medium containing one of the different biological materials into one of the delivery chambers of the apparatus, each propelling means when activated propelling a quantity of said fluid medium along a delivery path away from the associated orifice member; positioning the apparatus in relation to the receiving surface so that the orifice member is proximate the receiving surface and the delivery path for at least one selected fluid medium intersects the receiving surface at a locus of intersection; moving the apparatus in relation to the receiving surface so that the locus of intersection moves on the receiving surface; activating the propelling means associated with the orifice when the locus of intersection is at a first location on the surface onto which delivery of the selected fluid medium is desired; and repeating the moving and activating steps to deliver the plurality of different biological materials onto discrete locations on the surface.

In another general aspect the invention features a biomolecular array made using the apparatus of the invention or according to the method.

In another configuration, the invention features apparatus for delivering a plurality of different biological materials onto discrete locations on a surface, the apparatus comprising a generally planar substrate having a thickness and a contoured first surface and an edge, and a generally planar cover affixed to the first surface, the contoured first surface and the cover together defining a plurality of enclosed delivery chambers, a plurality of orifices on the edge, and a channel providing fluid communication between each chamber and at least one of the orifices; and common means for generating a pressure differential within at least two of the delivery chambers.

The apparatus of the invention is readily adaptable for automated handling of large numbers of different materials to make arrays of small dimensions and having a large number of array features.

Accordingly, in another general aspect the invention features a method for loading a plurality of different fluids into printing apparatus having a plurality of orifices in an orifice member, a plurality of delivery chambers each in fluid conducting relationship with at least one of the orifices, and means associated with each orifice for propelling fluid through the associated orifice from the delivery chamber that is in fluid conducting relationship with the orifice, and a vent for common venting at least two of the delivery chambers, the method comprising contacting the orifices with a fluid outside the delivery chamber and permitting the outside fluid to flow through the orifices into the delivery chambers. In some embodiments means for reducing pressure in the reservoirs is included, and can be operated to assist the flow of the fluid.

Preferably, where the apparatus is employed for construction of arrays having small dimensions and a high number of discrete array features in high density, the apparatus is part of a device that provides for suitable positioning of the deposition apparatus in relation to the receiving surface of the array substrate; for movement of the deposition apparatus in relation to the receiving surface as, for example, by scanning; and for activation of the propelling means at appropriate times during scanning or at appropriate locations to deposit the selected materials at the desired sites on the receiving surface. Portions or all of these functions can be automated and placed under microprocessor control employing suitable computer programs and user interface.

Other aspects and advantages of the invention will be apparent from the following detailed description, taken in conjunction with the accompanying drawings, illustrating by way of example the principles of the invention.

DRAWINGS

DETAILED DESCRIPTION

Figure 1A:
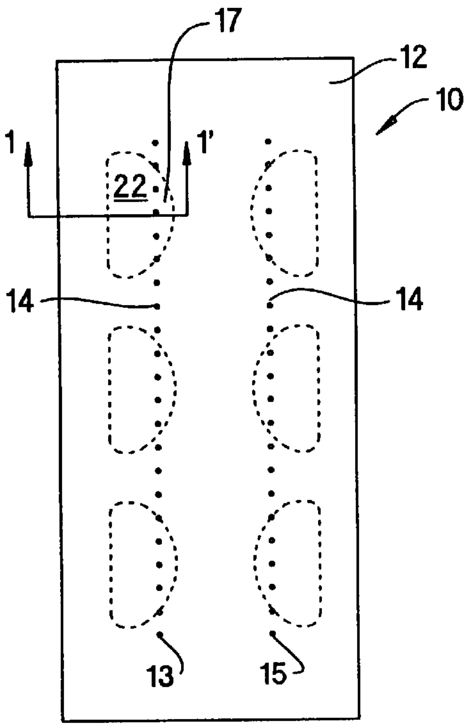
FIG. 1A is a sketch in plan view of an embodiment of multiple reservoir deposition apparatus according to the invention.

In general terms, the multiple-reservoir deposition apparatus of the invention according to various embodiments of the invention includes an orifice member and a back member and a barrier situated at least partly between them, so that the orifice member, the barrier member and the back member together define a number of delivery chambers. In each of the delivery chambers propelling means such as a heater or an electromechanical device is associated with each orifice in the orifice member such that when activated the propelling means causes a quantity of fluid to pass out through the orifice from the delivery chamber. In various embodiments of the invention, means common to at least two of the delivery chambers (and as many as all of them) are provided for generating a pressure differential within the chambers.

The description is here described in embodiments that include adaptations of devices employed in the printing industry and, particularly, of inkjet print heads and of automated devices for moving a print head over a print surface and for depositing the inks at the desired locations on the surface. Accordingly, reference to the inkjet printing art can be useful for understanding the apparatus of the invention and in understanding certain of the techniques useful in making certain of the components of the apparatus. The disclosures in the publications cited herein, above and below, are hereby incorporated herein by reference.

By way of example, inkjet devices employing thermal propelling means, and methods for their construction and use are described in U.S. Pat. Nos.: 5,772,829; 5,745,128; 5,736,998; 5,736,995; 5,726,690; 5,714,989; 5,682,188; 5,677,577; 5,642,142; 5,636,441; 5,635,968; 5,635,966; 5,595,785; 5,477,255; 5,434,606; 5,426,458; 5,350,616; 5,341,160; 5,300,958; 5,229,785; 5,187,500; 5,167,776; 5,159,353; 5,122,812; and 4,791,435. U.S. Pat. No. 5,658,802 notes that inkjet devices employing piezoelectric propelling means may be used for deposition of nucleic acids onto a substrate.

And, by way of example, conventional apparatus for moving a print head over a surface and controlling the deposition of inks are described in, for example, U.S. Pat. Nos. 5,772,829; 5,745,128; 5,736,998; 5,736,995; 5,726,690; 5,714,989; 5,682,188; 5,677,577; 5,642,142; 5,636,441; 5,635,968; 5,635,966; 5,595,785; 5,477,255; 5,434,606; 5,426,458; 5,350,616; 5,341,160; 5,300,958; 5,229,785; 5,187,500; 5,167,776; 5,159,353; 5,122,812; and 4,791,435.

Certain conventions will be employed to assist in the following detailed description of embodiments of the invention and with reference to the Figures. Particularly, the direction of movement of fluid as it is propelled out from a delivery chamber through an orifice or an orifice group toward a receiving surface, is here for illustrative purposes referred to as the "downstream" direction of flow; and some features of the device are accordingly "downstream" or "upstream" with respect to others. As the fluid is propelled through an orifice it exits the orifice on an outer or "front" surface of the orifice member, and thereafter is projected on a "delivery path" toward the receiving surface. Generally, the most downstream feature of the device is the exit end of the orifice at the outer surface of the orifice member; other features progressively further upstream from the exit end of the orifice are the delivery chamber, in which the propelling means are situated, the channel to the reservoir (if one is present) and the reservoir itself (if a reservoir separate from the delivery chamber is present). Portions of the device away from the outer surface of the orifice member are said to be toward the "rear" of the device. As will be appreciated, such conventions as "front" and "rear" are employed only for convenience and are not intended as limiting in any way.

Thus, in use, the device is positioned with the front surface of the orifice member facing the receiving surface and separated a small distance from it. After the delivery chamber (and reservoir, if any) have been loaded with the fluid, the fluid is said to form a fluid "column" constrained by the various surfaces of the device and having a (downstream) meniscus at some point at or within in the orifice, and an (upstream) meniscus at an upstream point in the delivery chamber (or in the channel or reservoir, if any). Increasing or decreasing the pressure over either meniscus can result in creating or changing a pressure differential in the fluid column.

The drawings showing embodiments of the apparatus are semidiagrammatic and not to scale and, particularly, some of the dimensions—particularly thicknesses—are for clarity of presentation shown greatly exaggerated in the Figures. Similarly, although the sectional views in the drawings for ease of description show the exit ends of orifices as oriented downward, this arrangement in the drawings is arbitrary and is not intended to suggest that the delivery path should necessarily be in a downward direction. Generally, the device can be operated in any orientation.

Figure 1B:
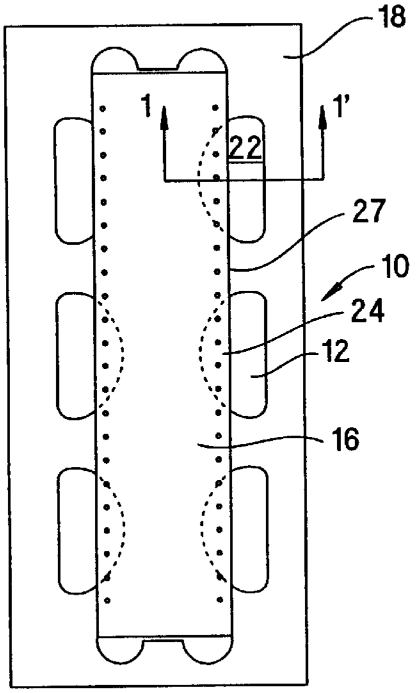
FIG. 1B is a sketch in plan view of the embodiment of FIG. 1A, seen from an opposing aspect.

Referring now to the Figures, FIGS. 1A, 1B show in plan view generally at 10 an embodiment of apparatus according to the invention having six reservoirs and six delivery chambers. In a front view, FIG. 1A, orifice member 12 (here an orifice plate) has orifices 14 disposed in two orifice rows 13, 15. Prototypes having this configuration were constructed having 150 orifices in each of the orifice rows. Rearward of orifice member 12 are a portion of barrier 20 (which is an adhesive layer), and, resting upon a portion of barrier 20 (which is an adhesive layer), reservoir block 18 and back member 16 (here a silicon die, as described more fully below), all more readily understood with reference to a rear view as in FIG. 1B and to a sectional view as in FIG. 1C.

In prototypes the delivery chambers (for example delivery chamber 17) are defined in part by the inner surface 11 of the orifice plate 12, in part by the front surface of the margin (for example surface 26) of the back member 16, and in part by an edge (for example edge 25) of the portion of the adhesive layer 20 situated between the orifice plate and the back member. And, in such prototypes, the reservoirs (for example reservoir 22), which are not separate from the delivery chambers, are defined in part by a portion of an edge of the back member (for example edge portion 27), and in part by an inner wall (for example wall 28) of the reservoir block 18 together with an edge (for example edge 29) of the adhesive layer, situated partly between the reservoir block 18 and the orifice plate 12.

A cover 19 (removed in FIG. 1B; shown in sectional view in FIG. 1C) is affixed to the rear surface of the reservoir block 18, and sealed peripherally (for example by means of an "O" ring 23) so that it provides a common enclosure for the reservoirs. Cover 19 is provided with a port 21, which by suitable connection (not shown in the Figures) can be joined to a source of increasing or decreasing pressure, by which a pressure differential can be commonly generated or existing pressure differentials commonly changed, in all the fluid columns at once. For example, connecting via the port 21 to a source of vacuum can provide for decreased pressure over the upstream meniscuses in all the reservoirs, resulting in a generally upstream movement of fluid in each of the orifices and delivery chambers. Any of a variety of commonly known types of increasing or decreasing pressure sources can be used; suitable vacuum sources, for example, include laboratory line vacuum and venturi apparatus. Preferably, the pressure can be regulated within defined limits, for example by valving or—in a venturi apparatus—by velocity control.

Figure 1C:
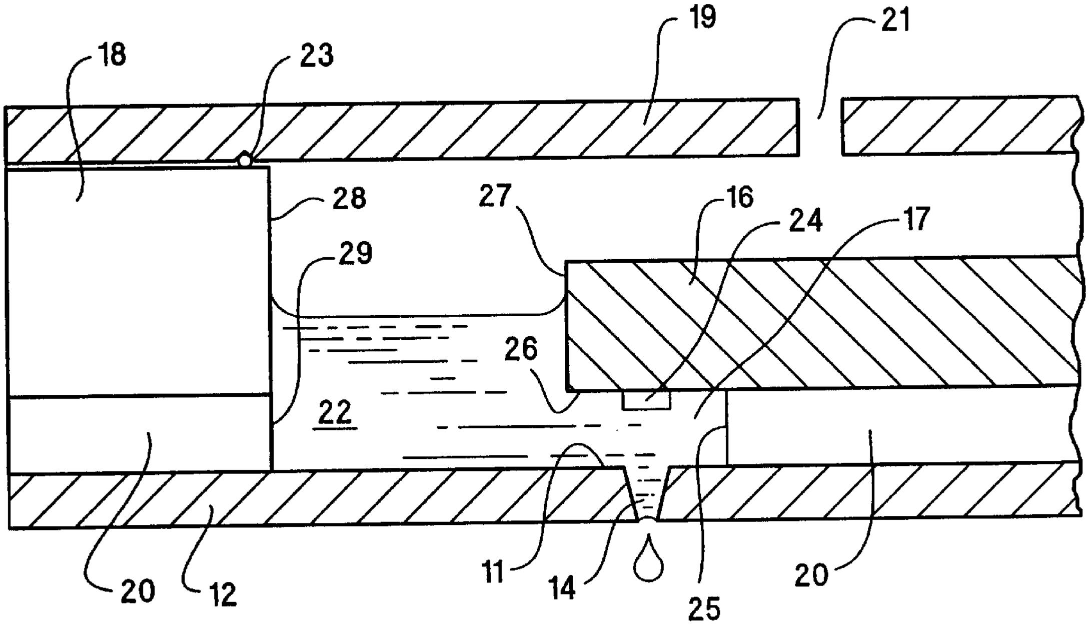
FIG. 1C is a sketch in sectional view thru 1–1' of the embodiment of FIG. 1A.

As will be appreciated, the delivery chambers and reservoirs of the device of FIGS. 1A, 1B, 1C can be filled with fluid by contacting the exit ends of the orifices with a quantity of the fluid and then lowering the pressure upstream from the orifices by connecting a source of vacuum at the port in the cover, resulting in drawing fluid in an upstream direction through the orifices into the delivery chambers and then into the reservoirs. Selected different fluids (or fluids containing different materials) can be drawn into the different chambers and reservoirs by contacting each orifice group (in fluid communication with a delivery chamber) with a different fluid.

Opposite each orifice 14 on the front surface 26 of the margin of the back member is the propelling means 24 (here an electrical resistor operating as a heating element), which is electrically connected to a source of electrical energy which can be controlled to deliver a suitable pulse of electricity to activate the propelling means on demand. (The connectors, the source of electrical energy, and the controller are not shown in the FIGS.) In a prototype of this embodiment the back member is a silicon die, and the electrical parts (heating element and connectors, for example) are formed using conventional solid state silicon ship manufacturing techniques.

In preferred embodiments the various fluid-handling parts of the apparatus of the invention generally have the following characteristics. The size of each orifice in the orifice plate is one that produces a spot of suitable dimensions on the substrate surface, where the orifice generally has an exit diameter (or exit diagonal depending upon the particular format of the device) in the range about 1 $\mu$m to 1 mm, usually about 5 $\mu$m to 100 $\mu$m, and more usually about 10 $\mu$m to 60 $\mu$m. The fluid capacity of the delivery chamber is in the range about 1 pL to 10 nL, usually about 10 pL to 5 nL and more usually about 50 pL to 1.5 nL. Where a reservoir is present, the combined fluid capacity of the reservoir and the connected delivery chambers is the range about 1 pL to 1 L, usually about 0.5 $\mu$L to 10 $\mu$L, and more usually about 1 $\mu$L to 5 $\mu$L. The front-to-rear thickness of the delivery chamber, defined by the space between the rear surface of the orifice plate and the front surface of the margin of the back plate, may in some embodiments be in the range less than about 100 $\mu$m, for example in prototypes of embodiments shown in the Figures herein, in the range 10 $\mu$m to 60 $\mu$m. These dimensions and the dimensions of the orifices are small enough that capillary forces can have a significant effect on the fluid pressures within the fluid column contained within these and larger fluid-handling parts. Particularly, an orifice and connected chamber so dimensioned can be expected to fill by capillary action when the orifice is brought into contact with the meniscus of a liquid; such filling can be particularly effective if the upstream end of the column is vented, as by leaving the reservoir open or by enclosing or by covering it but providing a vent to outside in the enclosure or cover. Similarly, where the reservoir is of large enough dimension that capillary forces within it are much smaller than in the delivery chamber and orifice, liquid can flow in the downstream direction by capillary action from the reservoir. The capillary-sized fluid handling parts and the larger parts work to provide a pressure differential within the liquid column, which can effect (or can assist in effecting) a movement of the capillary meniscus of the liquid. Thus, where the reservoir is open or is provided with a vent a pressure differential is established within liquid contained within the apparatus.

Where the propelling means is a heating element, the heating element will preferably be made out of a material that can deliver a quick energy pulse, and suitable materials include TaAl and the like. The thermal element is capable of achieving temperatures sufficient to vaporize a sufficient volume of the fluid in the firing chamber to produce a bubble of suitable dimensions upon actuation of the propelling means. Generally, the heating element is capable of attaining temperatures at least about 100° C., usually at least about 400° C., and more usually at least about 700° C., and the temperature achievable by the heating element may be as high as 1000° C. or higher.

A device as in FIGS. 1A, 1B, 1C, as in the embodiments described below, can be constructed by adaptation of techniques known in the printing art and, particularly, in the art of inkjet device construction. Certain elements of a prototype of the device of FIGS. 1A, 1B, 1C are adapted from parts of a commercially available thermal inkjet print head device available from Hewlett-Packard Co. as part no. HP51645A.

Figure 2A:
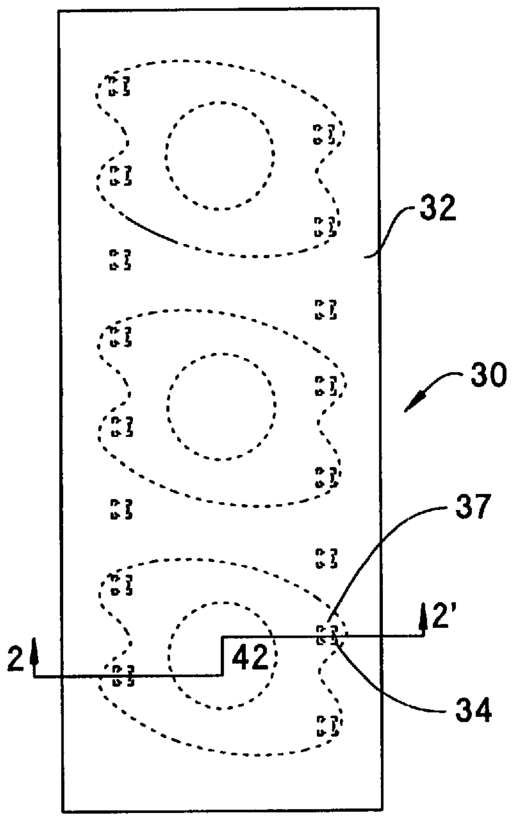
FIG. 2A is a sketch in plan view of a further embodiment of multiple reservoir deposition apparatus according to the invention.
Figure 2B:
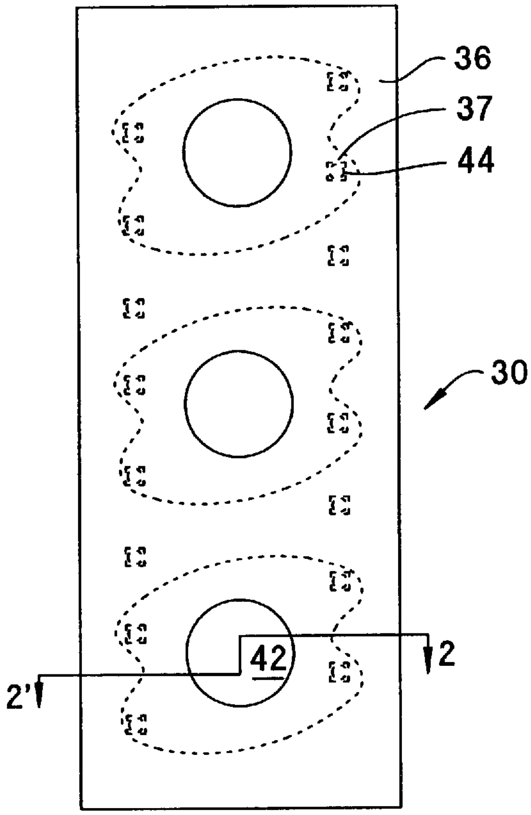
FIG. 2B is a sketch in plan view of the embodiment of FIG. 2A, seen from an opposing aspect.
Figure 2C:
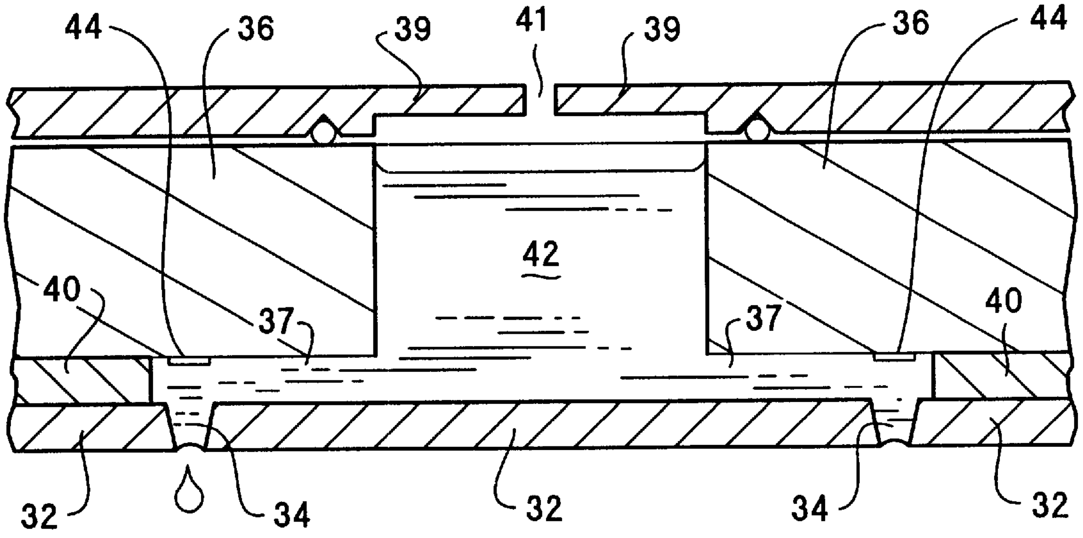
FIG. 2C is a sketch in sectional view thru 2–2' of the embodiment of FIG. 2A.

Referring now to FIGS. 2A, 2B, 2C, there is shown another embodiment of the apparatus of the invention, with plan views 2A, 2B and sectional view 2C laid out similarly to the views in FIGS. 1A, 1B, 1C respectively. In this embodiment there are three separate reservoirs, each in fluid communication with four delivery chambers each having an orifice and an associated propelling means.

Particularly, the apparatus, shown generally at 30, includes an orifice plate 32 with sixteen orifices (e.g., 34) in two staggered rows. Rearward of orifice plate 32 are barrier 40, and contacting barrier 40, back member 36 (a silicon die). The features are more readily understood by reference to the various views. In these embodiments the delivery chambers (for example 37) are defined by portions, together, of the inner surface of the orifice plate, the front surface of a margin of the back member, and an edge of the barrier. Each of the reservoirs (for example 42), which are not separate from the clusters of four delivery chambers they supply, is defined by the walls of an opening in the back member.

A cover 39 (shown in sectional view in FIG. 2C) is affixed to the rear surface of the back member 36, and is sealed so that it provides a common enclosure for all three reservoirs. Cover 39 is provided with a port 21, which by suitable connection (not shown in the Figures) can be joined to a source of increasing or decreasing pressure, by which a pressure differential can be generated or an existing pressure differential can be changed, in all sixteen fluid columns at once, as described with reference to FIGS. 1B, 1C, above.

The delivery chambers can be filled either by introducing fluids to the reservoirs through supply ports (not shown in the FIGS.) in the cover associated with each reservoir, and then as may be needed to force the fluids into the delivery chambers and to the orifices, raising the pressure over the fluid meniscuses in the reservoirs by closing the supply ports and raising the pressure at the port 21, or lowering the pressure at the orifices by sealing a source of vacuum to the front of the orifice plate and drawing a vacuum. Or, as described above, the fluids can be drawn into the different chambers and reservoirs by contacting each group of four orifices with a different fluid and then as may be needed to draw the fluids into the delivery chambers and the reservoirs, and reducing the pressure over the upstream meniscus by drawing a vacuum at the port 21. Or, in embodiments in which a reservoir is in fluid communication with more than one chamber (here, four) the reservoir may be filled with buffer, and then the selected fluids (which may be different or may contain different materials) can be drawn into the chambers through the orifices as described above, but only to the point where the respective chambers are filled and not to the point at which the different fluids can mix between adjacent chambers.

Opposite each orifice 34 on the front surface of the margin of the back member 36 is the propelling means 24 (here a heating element), which is connected to a source of electrical energy generally as described above.

Certain elements of a prototype of the device of FIGS. 2A, 2B, 2C are adapted from parts of a commercially available thermal inkjet print head device available from Hewlett-Packard Co. as part no. HP51649A.

Figure 3A:
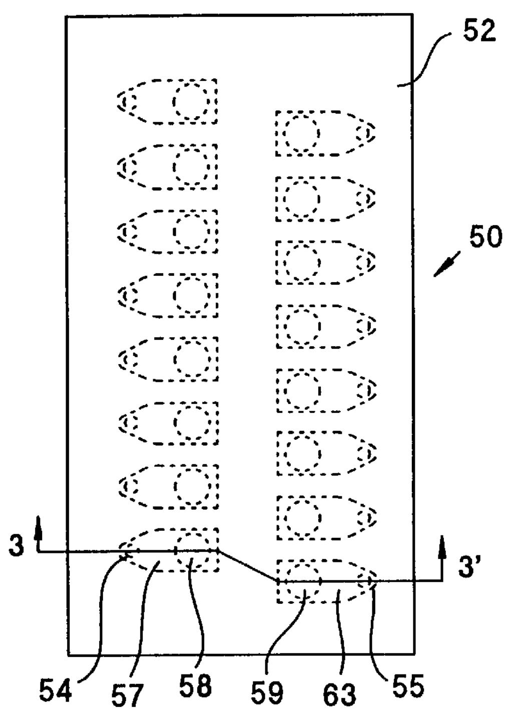
FIG. 3A is a sketch in plan view of a still further embodiment of multiple reservoir deposition apparatus according to the invention.
Figure 3B:
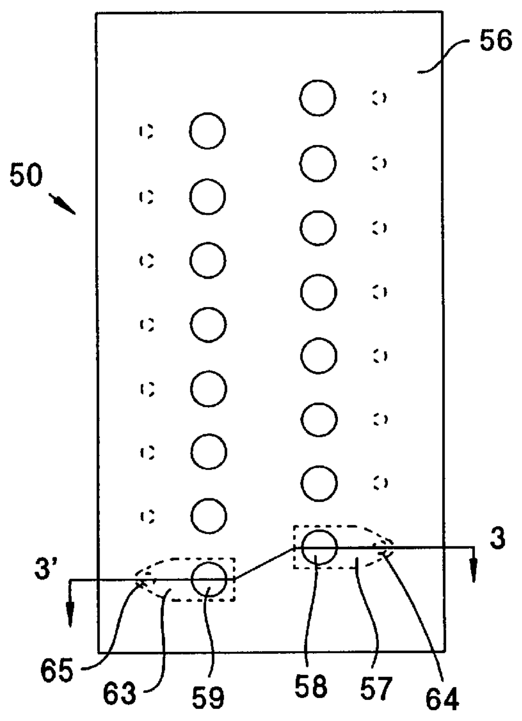
FIG. 3B is a sketch in plan view of the embodiment of FIG. 3A, seen from an opposing aspect.
Figure 3C:
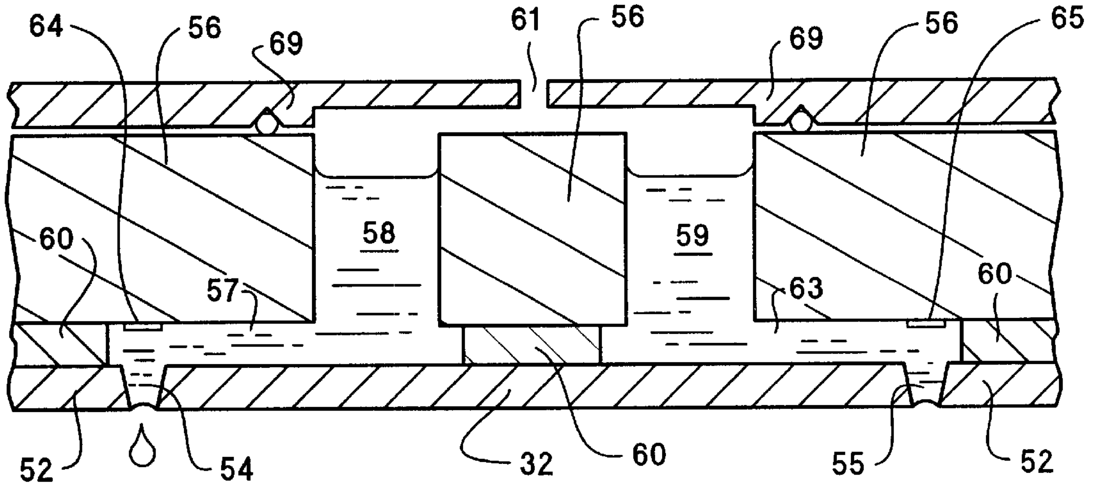
FIG. 3C is a sketch in sectional view thru 3–3' of the embodiment of FIG. 3A.

A further exemplary embodiment of the apparatus of the invention is shown in FIG. 3A, 3B, 3C, in which the respective views are laid out similarly to the views in the Figures above. In this embodiment there are sixteen separate reservoirs, each in fluid communication with a single delivery chamber each having an orifice and associated propelling means.

Particularly, the apparatus, shown generally at 50, includes an orifice plate 52 with sixteen orifices (e.g., 54, 55) in two staggered rows. Rearward of orifice plate 52 are barrier 60, and contacting barrier 60, back member 56 (a silicon die). The features are more readily understood by reference to the various views. In these embodiments the delivery chambers (for example 57, 63) are defined by portions, together, of the inner surface of the orifice plate, the front surface of a margin of the back member, and an edge of the barrier. Each of the reservoirs (for example 58, 59), which is separated from all the others but is not separate from the delivery chamber it supplies (respectively, for example, 57, 51), is defined by the walls of an opening in the back member.

A cover 69 (shown in sectional view in FIG. 3C) is affixed to the rear surface of the back member 56, and is sealed peripherally so that it provides a common enclosure for all sixteen reservoirs. Cover 69 is provided with a port 61, which by suitable connection (not shown in the Figures) can be joined to a source of increasing or decreasing pressure, by which a pressure differential can be changed or generated in all sixteen fluid columns at once, as described with reference to the Figures above.

As described with reference to embodiments above, the delivery chambers can be filled either by introducing fluids to the reservoirs through supply ports (not shown in the FIGS.) in the cover associated with each reservoir, and then as may be needed employing a pressure differential or change in pressure differential to force the fluids into the delivery chambers and to the orifices; or, the fluids can be drawn into the different chambers and reservoirs by contacting each orifice with a different fluid and then employing a pressure differential as may be needed to draw the fluids into the delivery chambers and the reservoirs.

Opposite each orifice 54, 55 on the front surface of a margin of the back member 56 is the propelling means, respectively 64, 65 (here a heating element), which is connected to a source of electrical energy generally as described above.

Certain elements of a prototype of the device of FIGS. 3A, 3B, 3C are adapted from parts of a commercially available thermal inkjet print head device available from Hewlett-Packard Co. as part no. HP51649A.

Figure 4A:
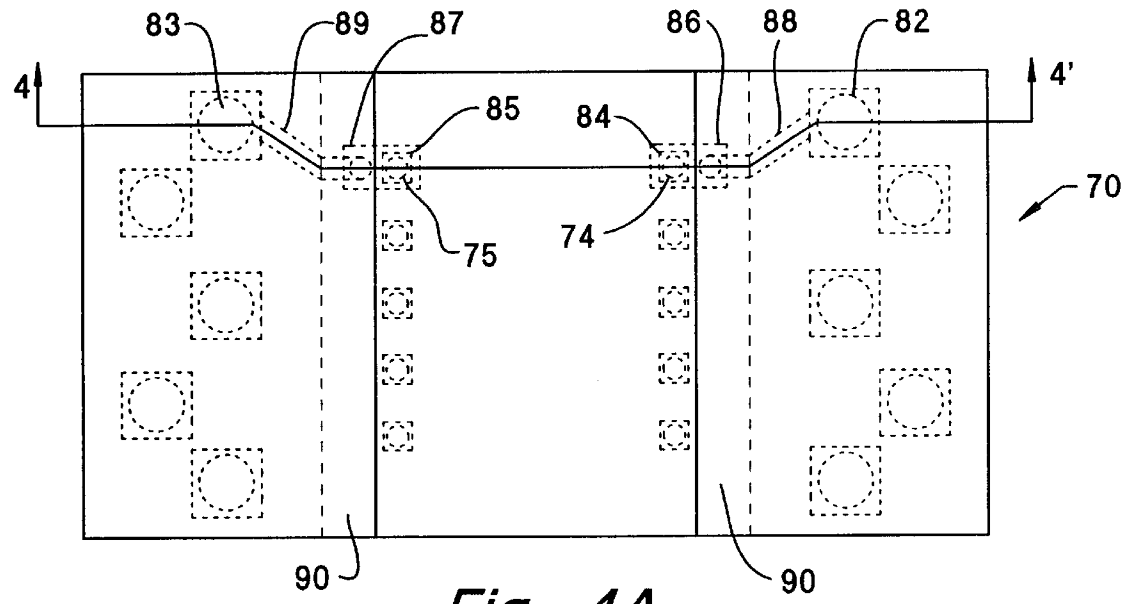
FIG. 4A is a sketch in plan view of a still further embodiment of multiple reservoir deposition apparatus according to the invention.
Figure 4B:
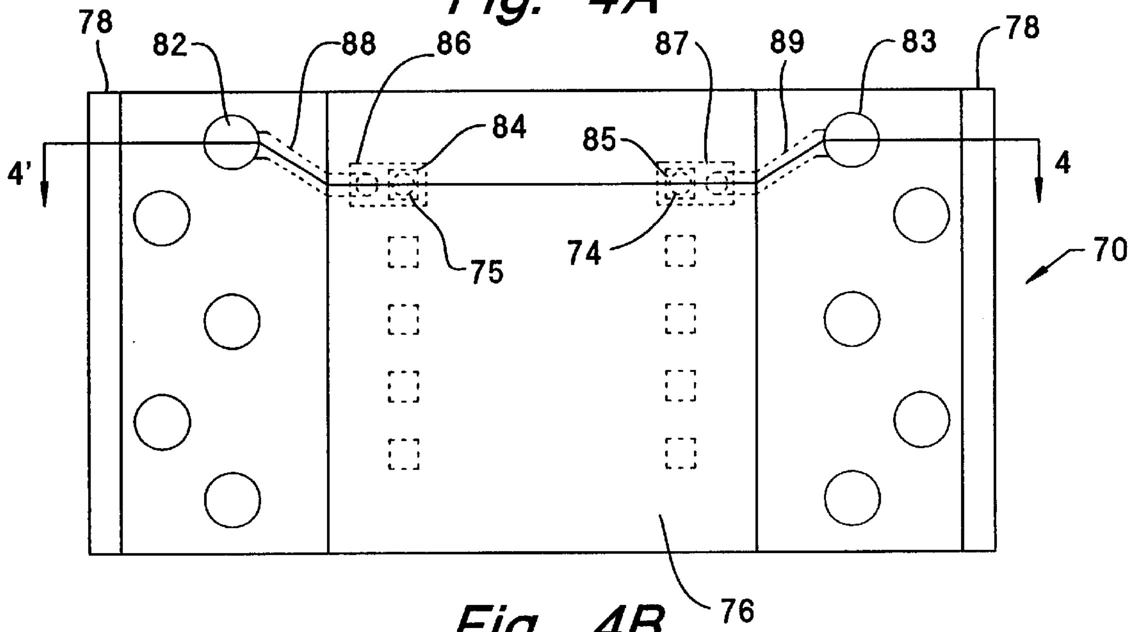
FIG. 4B is a sketch in plan view of the embodiment of FIG. 4A, seen from an opposing aspect.
Figure 4C:
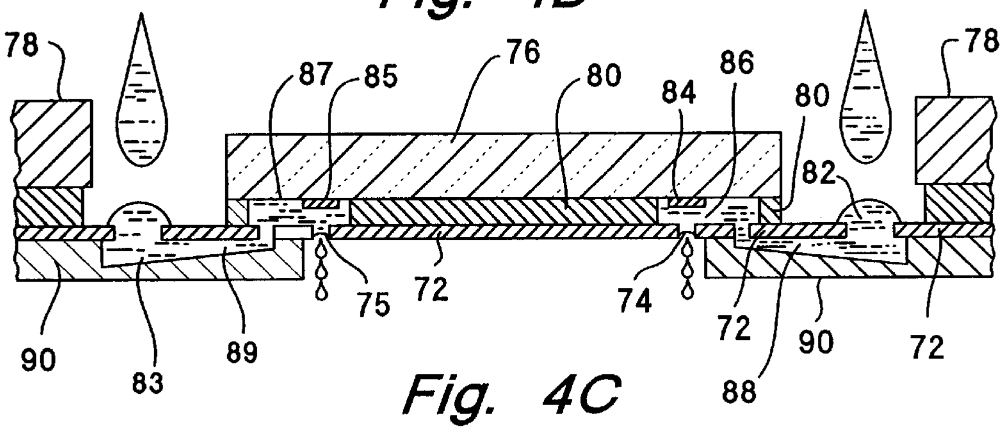
FIG. 4C is a sketch in sectional view thru 4–4' of the embodiment of FIG. 4A.
Figure 6A:
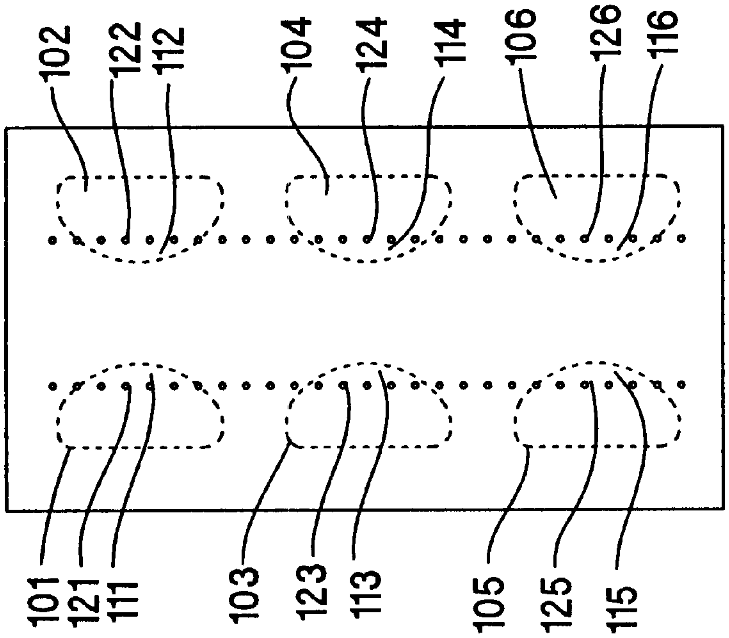
FIG. 6A is a sketch showing apparatus as in FIG. 1A, for reference in understanding the demonstration of Examples 2, 3.

Yet another exemplary embodiment is shown in FIGS. 4A, 4B, 4C in which the views are laid out generally as in the Figures above. In this embodiment there are ten delivery chambers each having an orifice and associated propelling means, and each connected by way of a channel to a separate reservoir, more or less remotely situated.

Particularly, the apparatus, shown generally at 70, includes an orifice plate 72 with ten orifices (e.g, 74, 75) in two rows. Rearward of orifice plate 72 are barrier 80 and back member 76 (a silicon die). The features are more readily understood by reference to the various views. In these embodiments the delivery chambers (for example 86, 87) are defined by portions, together, of the inner surface of the orifice plate, the front surface of a margin of the back member, and edges of the barrier. Each of the reservoirs is here separate from the delivery chamber with which it communicates (although in fluid communication with it, as described below), and may in some embodiments be situated remotely from the delivery chamber.

The delivery chambers can be filled either by introducing fluids to the reservoirs through supply ports (not shown in the FIGS.) in the cover associated with each reservoir, and then as may be needed to force the fluids into the delivery chambers and to the orifices, raising the pressure over the fluid meniscuses in the reservoirs by closing the supply ports and raising the pressure at the port 21, or lowering the pressure at the orifices by sealing a source of vacuum to the front of the orifice plate and drawing a vacuum. Or, as described above, the fluids can be drawn into the different chamber and reservoirs by contacting each orifice with a different fluid and then as may be needed to draw the fluids into the delivery chambers and the reservoirs, and reducing the pressure over the upstream meniscus by drawing a vacuum at the port 21.

Opposite each orifice (e.g., 74, 75) on the front surface of a margin of the back member 76 is a propelling means (e.g., respectively, 84, 85; here heating elements), which is connected to a source of electrical energy generally as described above.

In this embodiment the reservoirs (e.g., 82, 83) are in fluid communication with their respective delivery chambers (e.g., 86, 87) by way of channels (e.g., 88, 89) each having an opening both to it respective delivery chamber and to its respective reservoir. In the embodiment shown here, the channels are formed within a member 90 affixed to the front surface of the orifice plate 72. Where the delivery chambers, connecting channels and openings to the reservoirs have sufficiently small dimensions, the contents of each reservoir are constrained about the opening by the surface tension of the fluid, as illustrated diagrammatically in FIG. 4C.

Apparatus according to this embodiment may preferably be loaded by introducing the different materials from the rear. Because the reservoirs are remotely situated, they may arranged in any desirable configuration and may be spaced apart from one another at any desired distance, irrespective of the spacing and the configuration of the delivery chambers and their respective orifices. Accordingly, the orifices may be very closely spaced and may be arranged in a pattern designed to facilitate construction of the desired array features, while the reservoirs may be arranged and dimensioned in a manner designed to facilitate transfer of sample materials. Suitable arrangements for the reservoirs might be matched to conventional transfer apparatus, for example; or to conventional preparative trays such as microtitre plates, for example.

As will be appreciated, the channels connecting the reservoirs to the respective delivery chambers can be formed in any of a variety of ways other than as shown by way of example in FIG. 4C. Manufacturing concerns may likely determine which way may be employed for a particular device. Formation of the channels in front of the plane of the orifices, as shown in the Figure, provides a ready approach, easily manufactured by forming a number of grooves at the appropriate positions in a surface of a thin sheet and then affixing that surface of the sheet in a sealed relation onto the front surface of the orifice member.

The apparatus of the invention may be used to construct an array of biological materials on a receiving surface of an array substrate in a manner analogous to printing a pattern of pigmented inks onto a print surface, and the techniques and devices for positioning and moving the apparatus in relation to the receiving surface, and for propelling the selected materials onto the surface to provide the desired pattern of array features, can be adapted from techniques and devices generally known in the inkjet printing art. Here, rather than delivering a pigmented ink onto the surface, the delivery chamber delivers a selected biological material, or a fluid medium containing a selected biomolecule.

Biomolecular arrays may be constructed according to the invention having array features presenting any desired biomolecules, including natural and synthetic proteins and peptides including polypeptides and oligopeptides and fragments and derivatives; natural and synthetic nucleic acids (ribonucleic acids and deoxyribonucleic acids and derivatives) including single and double stranded polynucleotides and oligonucleotides and fragments and derivatives; and the like. According to the invention, complex biopolymers or oligomers can be collected or synthesized remotely from the device and then deposited onto the surface; or can be constructed in situ by sequential reactions on the array surface, where the components of the reactions can be serially provided by deposition using the apparatus of the invention.

In practicing the invention for generating a nucleic acid array by deposition of nucleic acids, each delivery chamber from which material is to be delivered is loaded with an aqueous nucleic acid composition or fluid. By aqueous composition is meant a fluid of at least water and nucleic acid molecules, and the aqueous nucleic acid composition may also contain one or more additional agents, including: buffering agents, salts, metal cations, enzymes, etc., where such agents may be present in the composition as a result of the way in which the composition is prepared. For example, where the nucleic acid composition is prepared via preparative PCR techniques, the aqueous composition that is loaded into the inkjet head may contain, in addition to water and the PCR produced product DNA, buffers, dNTPs, polymerase, salts, left over primers, and the like. The nucleic acid fluid compositions may be prepared in a number of different ways. Thus, the nucleic acid may be synthesized using phosphoramidite synthesis technology, preparative PCR, purification from naturally occurring sources, and the like, where such methods are well known to those of skill in the art.

The nucleic acid of the aqueous nucleic acid composition may vary considerably. Accordingly, the nucleic acid may be DNA, RNA or some other synthetic type of nucleic acid in which the conventional backbone has been replaced with a non-naturally occurring or synthetic backbone, e.g., PNA and the like, and can be a nucleic acid in which one or more of the conventional bases has been replaced with a synthetic base capable of participating in Watson-Crick type hydrogen bonding interactions. The length of the nucleic acid will be chosen according to characteristics of the article to be prepared using the subject method, e.g., the nature of the nucleic acid array to be produced. Thus, for example, the nucleic acid may be an oligonucleotide or a polynucleotide. Of particular interest is the use of the subject methods to deposit polynucleotides on the surface of a substrate. Generally, as the terms are used herein, a polynucleotide is a polymer of nucleotides that is at least about 100 nt in length, usually at least about 120 nt in length and more usually at least about 150 nt in length, where the polynucleotide may be a long as 8,000 nt in length or longer, but in many embodiments will not exceed about 3,000 nt. The nucleic acid in many embodiments of particular interest is cDNA.

The nucleic acid composition or fluid may be loaded into the firing chamber and fluid reservoir using any convenient means. Following loading of the nucleic acid fluid into the deposition device, it may be desirable to "prime" the device prior to use. One means of priming the device is to apply sufficient pressure to the fluid in the reservoirs, by way of the vent, or to draw a vacuum at the orifices, so that a volume of fluid is forced out through the orifices. However, where it is desirable to minimize waste of the fluid containing the biological material, such as where the fluid is costly or is in limited supply, it may be preferred to load the delivery chamber in an upstream direction through the orifice, as described above. A pressure differential suitable for loading the apparatus is typically at least about 5 inches of water, and may be at least about 10 inches of water and as great as about 100 inches of water or greater.

For deposition the apparatus is positioned so that the front surface of the orifice member is in opposing relation to and at a suitable distance from the receiving surface of the substrate. The distance between the orifice and the substrate surface will not be so great that the volume of expelled fluid cannot reach the substrate surface and there be deposited in a reproducible manner; nor will it be so small that interference between the apparatus and the receiving surface can interfere as one moves with respect to the other. Accordingly, the apparatus generally is operated with the orifice a distance apart from the substrate surface in the range about 10 $\mu$m to 10 mm, usually about 100 $\mu$m to 2 mm, and more usually about 200 $\mu$m to 1 mm.

The propelling means associated with a particular orifice is activated when the delivery path intersects a location on the receiving surface where deposition of the fluid contained in the particular delivery chamber behind that orifice is desired. Different locations on the receiving surface are brought into the various delivery paths by moving the delivery apparatus in relation to the surface; this may of course be accomplished by immobilizing the array substrate and moving the deposition apparatus or by holding the deposition apparatus in place and moving the array substrate, or by some combination of these. The propelling means is activated by electrical control, and activation of individual means can be coordinated with the relative movement (or with the relative position) of the orifice and the surface.

Where the propelling means is an electrically resistive heating element, activation results in raising the temperature of the heater to a temperature sufficient to vaporize a portion of the fluid immediately adjacent the heater and produce a bubble. The temperature of the heater is raised to a temperature at least about 100 ° C., usually at least about 400 ° C. and more usually at least about 700° C., and the temperature may be raised as high as 1000° C. or higher, but is usually raised to a temperature that does not exceed about 2000° C. and more usually does not exceed about 1500° C. Accordingly, a sufficient amount of energy will be delivered to the resistive element to produce the requisite temperature rise, where the amount of energy is generally in the range about 1.0 to 100 $\mu$J, usually about 1.5 to 15 $\mu$J. The portion of fluid in the firing chamber that is vaporized will be sufficient to produce a bubble in the firing chamber of sufficient volume to force an amount of liquid out of the orifice.

The formation of the bubble in the firing chamber traps a portion or volume of the fluid present in the firing chamber between the heating element and the orifice and forces an amount or volume of fluid out of the orifice at high speed. The amount or volume of fluid that is forced out of the firing chamber can be controlled according to the quantity of biological material to be deposited at the particular location on the receiving surface. As is well known in the ink jet print art, the amount of fluid that is expelled in a single activation event can be controlled by changing one or more of a number of parameters, including the orifice diameter, the orifice length (thickness of the orifice member at the orifice), the size of the deposition chamber, and the size of the heating element, among others. The amount of fluid that is expelled during a single activation event is generally in the range about 0.1 to 1000 pL, usually about 0.5 to 500 pL and more usually about 1.0 to 250 pL. A typical velocity at which the fluid is expelled from the chamber is more than about 1 m/s, usually more than about 10 m/s, and may be as great as about 20 m/s or greater. As will be appreciated, if the orifice is in motion with respect to the receiving surface at the time the propelling means is activated, the actual site of deposition of the material will not be the location that is at the moment of activation in a line-of-sight relation to the orifice, but will be a location that is predictable for the given distances and velocities.

Upon actuation of the propelling means, as described above, fluid is expelled from the orifice and travels to the substrate surface, where it forms a spot on the substrate surface. In this manner, the biological material (such as, e.g., a nucleic acid) is deposited on the substrate surface. As mentioned above, by varying the operating parameters of the apparatus, the spot dimensions can be controlled such that spots of various sizes can be produced. The sizes of the spots (and, hence, of the array features) can have widths (that is, diameter, for a round spot) in the range from a minimum of about 10 $\mu$m to a maximum of about 1.0 m. In embodiments where very small spot sizes or feature sizes are desired, material can be deposited according to the invention in small spots whose width is in the range about 1.0 $\mu$m to 1.0 mm, usually about 5.0 $\mu$m to 500 $\mu$m, and more usually about 10 $\mu$m to 200 $\mu$m.

Where a pattern of array features is desired, any of a variety of geometries may be constructed, including for example, organized rows and columns of spots, e.g., a grid of spots, across the substrate surface, a series of curvilinear rows across the substrate surface, e.g., a series of concentric circles or semi-circles of spots, and the like. An array according to the invention generally includes at least tens of features, usually at least hundreds, more usually thousands, and as many as ten thousand or more features. Where a pattern of spots is deposited on a substrate surface, the pattern may vary as desired. As such, the pattern may be in the form of organized rows and columns of spots, e.g. a grid of spots, across the substrate surface, a series of curvilinear rows across the substrate surface, e.g. a series of concentric circles or semi-circles of spots, and the like.

The subject methods and devices may be used to deposit biomolecules on surfaces of any of a variety of different substrates, including both flexible and rigid substrates. Preferred materials provide physical support for the deposited material and endure the conditions of the deposition process and of any subsequent treatment or handling or processing that may be encountered in the use of the particular array.

The array substrate may take any of a variety of configurations ranging from simple to complex. Thus, the substrate could have generally planar form, as for example a slide or plate configuration, such as a rectangular or square or disc. In many embodiments, the substrate will be shaped generally as a rectangular solid, having a length in the range about 4 mm to 200, usually about 4 mm to 150 mm, more usually about 4 mm to 125 mm; a width in the range about 4 mm to 200 mm, usually about 4 mm to 120 mm and more usually about 4 mm to 80 mm; and a thickness in the range about 0.01 mm to 5.0 mm, usually from about 0.1 mm to 2 mm and more usually from about 0.2 to 1 mm. The configuration of the array will be selected according to manufacturing, handling, and use considerations.

The substrates may be fabricated from any of a variety of materials. In certain embodiments, such as for example where production of binding pair arrays for use in research and related applications is desired, the materials from which the substrate may be fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, may be particularly useful in this embodiment. For rigid substrates, specific materials of interest include: glass; plastics, e.g., polytetrafluoroethylene, polypropylene, polystyrene, polycarbonate, and blends thereof, and the like; metals, e.g., gold, platinum, and the like; etc.

The substrate surface onto which the nucleic acid composition is deposited may be smooth or substantially planar, or have irregularities, such as depressions or elevations. The surface may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof, e.g., peptide nucleic acids and the like; polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto, e.g., conjugated.

EXAMPLE 1

This Example demonstrates use of a multiple reservoir deposition device for deposition of cDNA onto a discrete location on a glass substrate.

Figure 5A:
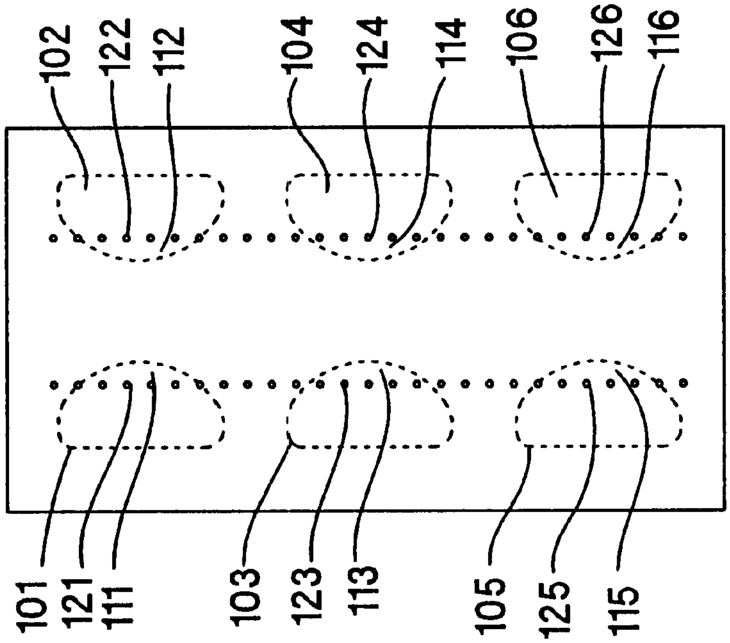
FIG. 5A is a sketch showing apparatus as in FIG. 1A, for reference in understanding the demonstration of Examples 1, 3.

The device was constructed generally as described with reference to FIGS. 1A, 1B. As constructed the device had six delivery chambers each in fluid communication with one of six reservoirs, and each delivery chamber was in fluid communication with a group of several orifices in an orifice row. The arrangement is shown diagrammatically in FIG. 5A, in which for the first through sixth sets of reservoirs, chambers and orifices are for reference herein arbitrarily numbered 101 through 106 (reservoirs) 111 through 116 (chambers) and 121 through 126 (groups of orifices) respectively. As described with reference to FIGS. 1A, 1B the orifices are formed as two parallel rows of openings through the orifice plate, about 150 openings in each row, and application of the barrier both isolates adjacent chambers and blocks all the openings except for those that are within the chambers. Each delivery chamber is in fluid conducting relationship with about ten or more unblocked orifices.

A $^{32}$p cDNA was constructed according to standard procedures. Briefly, a 500 base pair double-stranded DNA containing vector and hepatitis C virus sequences was generated and $^{32}$P-labeled by Polymerase Chain Reaction techniques using sequence-specific primers, a plasmid template containing hepatitis C virus sequences in the vector pSP64 (Promega), and $^{32}$P-dATP. Taq Gold enzyme (Perkin Elmer) was used for the PCR according to manufacturer's instructions. The 500 base pair DNA product from the PCR reaction was purified from unincorporated $^{32}$P-dATP using an Amicon microfiltration unit Then a 1 $\mu$L sample of the $^{32}$P cDNA was introduced into delivery chamber 114 as follows. First a cover, having a port to vacuum, was applied in sealed relationship to the open reservoirs. Then a droplet of fluid containing the $^{32}$P cDNA was contacted with orifice group 124, and vacuum was briefly applied to the port to draw the fluid through the orifices into delivery chamber 114 and then, as the delivery chamber filled, into reservoir 104. Then the vacuum was relieved.

Figure 5B:
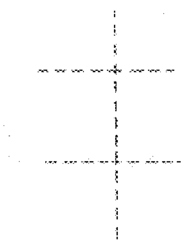
FIGS. 5B and 5C are prints of radiograms produced in the demonstration of Example 1.

The print head was then positioned over the receiving surface of a glass slide, and the heaters associated with all the orifices were activated 500 times in succession to propel labeled cDNA (from orifice group 124) toward the receiving surface. FIG. 5B is a diagrammatic sketch of a portion of the receiving surface of the glass slide; in the sketch broken lines show approximate bounds within which the deposition sites 131 through 136 are located.

Figure 5C:
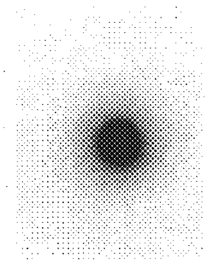

The surface, bearing the deposited materials, was then treated radiographically according to standard procedures. The resulting radiogram is shown in FIG. 5C, onto which the sketch of FIG. 5B is superimposed for reference. The radiogram shows that there was detectable label (5x10$^6$ units) at deposition site 134, which received labeled cDNA propelled through orifice group 124 from delivery chamber 114, and substantially no detectable label at any of the other five sites.

EXAMPLE 2

This Example illustrates use of a multiple reservoir deposition device for deposition of cDNAs onto adjacent discrete locations on a glass substrate.

Figure 6B:
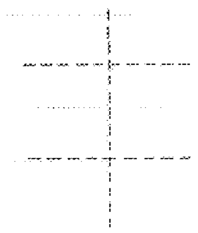
FIGS. 6B and 6C are prints of radiograms produced in the demonstration of Example 2.

The device constructed in Example 1, above, was employed in this Example as well. Following completion of the demonstration described in Example 1, the reservoirs, delivery chambers and orifices were washed by repeated flushing with buffer (2×SSPE+Triton) through a wash port in the cover. Then a 1 $\mu$L sample of a $^{32}$P cDNA constructed as described in Example 1 was introduced by way of orifice groups 123 and 124 into each of delivery chambers 113 and 114 and then into reservoirs 103 and 104. In a similar manner, delivery chambers 111, 112, 115 and 116 and reservoirs 101, 102, 105 and 106 were loaded with cold buffer (3×SSC) through the respective orifice groups. The print head was then positioned over the receiving surface of a glass slide, and the heaters associated with all the orifices were activated 500 times in succession to propel labeled cDNA (from each of orifice groups 123 and 124) and buffer (from orifice groups 121, 122, 125 and 126) toward corresponding locations on the receiving surface. FIG. 6B is a diagrammatic sketch of a portion of the receiving surface of the glass slide; in the sketch broken lines show approximate bounds within which the deposition sites 131 through 136 are located.

Figure 6C:
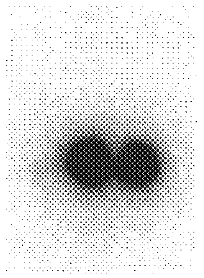

The surface, bearing the deposited materials, was then treated radiographically according to standard procedures. The resulting radiogram is shown in FIG. 6C, onto which the sketch of FIG. 6B is superimposed for reference. The radiogram shows that there was detectable label (6x10$^6$ units) at deposition sites 133 and 134, which received labeled cDNA propelled through orifice groups 123 and 124 from delivery chambers 113 and 114, respectively, and substantially no detectable label at any of the other four sites.

EXAMPLE 3

This Example demonstrates that a multiple reservoir deposition device according to the invention can be effectively washed of sample by repeated flushing following use for deposition of cDNA onto discrete locations on a glass substrate.

Figure 5D:
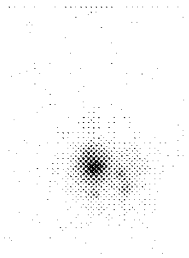
FIGS. 5D–5F are prints of radiograms produced in the demonstration of Example 3.

Following the demonstration described in Example 1, the reservoirs were washed by flushing them with 1 mL buffer (2×SSPE+Triton) introduced into the reservoirs by way of a wash port in the cover. All six reservoirs were then loaded with cold buffer (3×SSC), the print head was positioned over a fresh glass slide, and the heaters were activated 500 times in succession to propel fluid from all the reservoirs onto corresponding locations on the receiving surface. A radiogram from the receiving surface (FIG. 5D) shows that label was detectable in fluid deposited at site 134, but at a much reduced level (1x10$^5$ units).

Figure 5E:
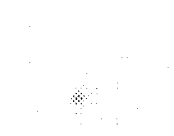
Figure 5F:

This sequence: wash—load with buffer—print was repeated on another fresh glass slide. A radiogram from the receiving surface (FIG. 5E) shows label detectable in fluid deposited at site 134 at a still further reduced level (6x10$^3$ units). A third repetition of the sequence: wash load with buffer—print yielded the radiogram shown in FIG. 5F again showing label detectable in fluid deposited at site 134 nearly 1000 fold lower (8x10$^3$ units) than in the initial deposition of labeled cDNA.

The print head was washed three additional times before using the print head for the demonstration of Example 2. In these washes the wash liquid was forced under pressure through the orifices.

Following the demonstration described in Example 2, the sequence: wash—load with buffer—print as described above was carried out first, second, and third times, each on a fresh receiving surface of a glass slide. These yielded the radiograms shown in FIGS. 6D, 6E and 6F, respectively. After one wash (FIG. 6D), label was detectable at reduced levels in fluids deposited at sites 133 ($2\times10^4$ units) and 134 ($4\times10^4$ units); after two washes (FIG. 6E), label was detectable in fluids deposited at both site 133 and 134, but at further reduced levels ($1\times10^4$ units); and after three washes label was detectable at levels ($2\times10^3$ units at site 133; $3\times10^3$ units at site 134) lower by more than 1000 fold than in the initial deposition of cDNA from chambers 113 and 114.

Figure 6D:
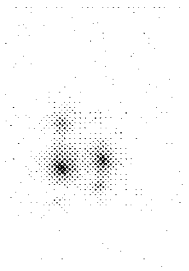
FIGS. 6D–6F are prints of radiograms produced in the demonstration of Example 3.
Figure 6E:
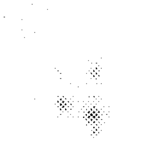
Figure 6F:
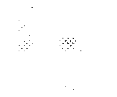
Figure 7A:
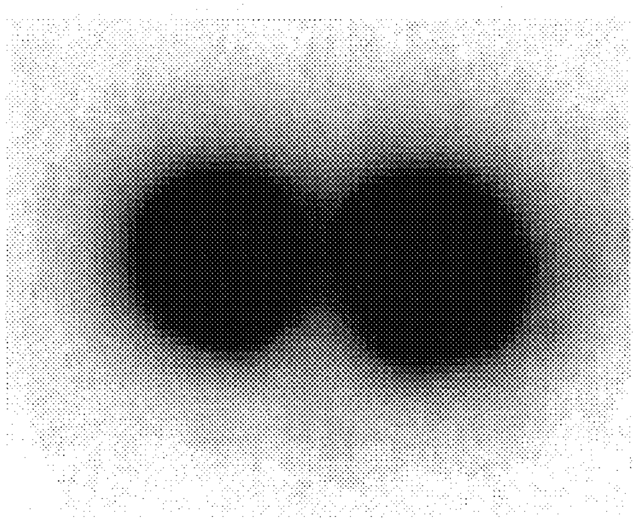
FIGS. 7A–7B are the prints shown in FIGS. 6C and 6D, enlarged.
Figure 7B:
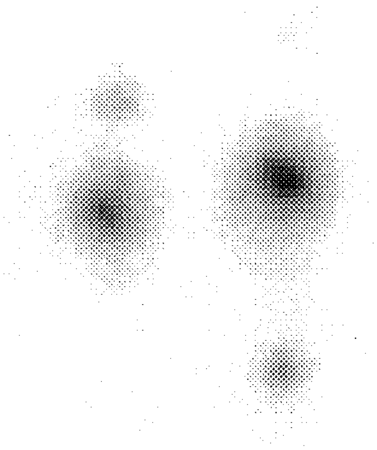

The radiograms of FIGS. 6C and 6D are reproduced in six-fold magnification, in FIGS. 7A, 7B. In FIG. 7B, some degree of cross-contamination to sites 131, 132, 135 and 136 appears; this resulted from the reservoirs having been filled to overflowing during the wash, allowing contaminated wash fluid to flow from reservoirs 103 and 105 into adjacent reservoirs. This shows that cross-contamination is detectable under the conditions of these demonstrations. No cross-contamination appears in sites 131, 132, 135 or 136 of FIG. 7A, demonstrating that the cDNAs propelled from adjacent delivery chambers 113 and 114 were successfully deposited onto discrete locations on the slide, even though the heaters were repeatedly activated to propel material 500 times in succession toward the same sites.

From the foregoing it will be appreciated that the multiple reservoir apparatus according to the invention for constructing biomolecular arrays is uncomplicated and readily automated, and provides for reduced waste of materials and can result in efficient and reproducible rapid fabrication of versatile and reliable arrays.

Although several specific embodiments of the invention have been described and illustrated, the invention is not to be limited to specific forms or arrangements of parts so described and illustrated. The invention is limited only by the following claims.

We claim:

1. Apparatus for delivering a plurality of different biological materials onto discrete locations on a receiving surface, the apparatus comprising:

a plurality of orifices in a one-piece orifice member;

a plurality of delivery chambers each in fluid conducting relationship with at least one of said orifices;

at least six reservoirs each in fluid conducting relationship with at least one of said delivery chambers;

means associated with each orifice for propelling fluid through the associated orifice from the delivery chamber that is in fluid conducting relationship with the orifice; and a vent for commonly venting the at least six reservoirs;

the apparatus further comprising means for contacting at least one of said orifices with a fluid outside said delivery chamber whereby said fluid will flow from outside the orifice, through the orifice and into the delivery chamber.

2. The apparatus of claim 1 wherein the combined capacity of each said reservoir and delivery chamber in fluid conducting relationship therewith is less than 100 microliters.

3. The apparatus of claim 2 wherein the combined capacity of each said reservoir and delivery chamber in fluid conducting relationship therewith is less than 10 microliters.

4. The apparatus of claim 2 wherein the combined capacity of each said reservoir and delivery chamber in fluid conducting relationship therewith is less than 1 microliter.

5. The apparatus of claim 1, comprising at least sixteen said reservoirs.

6. The apparatus of claim 1, comprising at least fifty said reservoirs.

7. The apparatus of claim 1, comprising at least one hundred said reservoirs.

8. The apparatus of claim 1, further comprising means operatively connected with said vent for commonly changing the pressure within said at least six reservoirs.

9. The apparatus of claim 8 wherein said pressure changing means comprises means for reducing pressure within said at least six reservoir.

10. The apparatus of claim 9, whereby operating said pressure reducing means results in drawing the fluid through said orifice into said delivery chamber.

11. The apparatus of claim 8 wherein said pressure changing means comprises means for increasing pressure within said at least six reservoirs.

12. The apparatus of claim 11 wherein said pressure increasing means comprises means for introducing a fluid into said at least six reservoirs, whereby operating said pressure increasing means results in expelling fluid out from said at least one delivery chamber in fluid communication with said reservoir by way or said orifices.

13. The apparatus of claim 1 wherein said propelling means comprises a source of heat.

14. The apparatus of claim 13 wherein said source of heat comprises an electrical heater, said heater being operative when activated to heat fluid within the delivery chamber to a degree sufficient to propel a quantity of fluid out from the delivery chamber through the associated orifice.

15. The apparatus of claim 1 wherein said means for propelling comprises a piezoelectric device.

16. The apparatus of claim 1 wherein said orifice member is a planar orifice plate having an inner surface and an exit surface, said orifices providing openings through said plate from said inner surface to said outer surface.

17. The apparatus of claim 1, comprising a plurality of said orifice members.

18. A method for delivering a plurality of different biological materials onto discrete locations on a receiving surface, the method comprising:

loading a fluid medium containing one of said different biological materials through the orifice and into one of said delivery chambers of the apparatus of claim 10, each said means for propelling when activated propelling a quantity of said fluid medium along a delivery path away from said orifice member;

positioning the orifices, delivery chambers, reservoirs and means for propelling of the apparatus of claim 10 in relation to the receiving surface whereby said orifice member is proximate the receiving surface and the delivery path for said fluid medium intersects said receiving surface at a locus of intersection;

moving the orifices, delivery chambers, reservoirs and means for propelling of the apparatus of claim 10 in relation to the receiving surface so that locus of intersection moves on said receiving surface;

activating the means for propelling associated with said orifice when the locus of intersection is at a first location on said surface onto which delivery of the selected said fluid medium is desired; and repeating the moving and activating steps to deliver the plurality of different biological materials onto discrete locations on the surface.

19. The method of claim 18 wherein said fluid medium loading step results in each said delivery chamber being loaded with a fluid containing a different biological material.

20. The method of claim 18 wherein said plurality of different biological materials comprises a plurality of nucleic acids.

21. The method of claim 20 wherein said plurality of nucleic acids comprises a plurality of nucleic acids selected from the group consisting of DNAs, RNAs and synthetic derivatives thereof.

22. A method according to claim 18 wherein the fluid medium loading comprises contacting at least one of said orifices with a fluid outside said delivery chamber.

23. A method according to claim 22 wherein the fluid medium loading comprises applying a reduced pressure through the vent to commonly reduce the pressure within at least six reservoirs.

24. A method according to claim 22 wherein the orifice member is a planar orifice plate having an inner surface and an exit surface, said orifices providing openings through said plate from said inner surface to said outer surface.

25. A method according to claim 23 wherein the orifice member is a planar orifice plate having an inner surface and an exit surface, said orifices providing openings through said plate from said inner surface to said outer surface.

26. Apparatus for delivering a plurality of different biological materials onto discrete locations on a receiving surface, the apparatus comprising:

a plurality of orifices in a one-piece orifice member;

a plurality of delivery chambers each in fluid conducting relationship with at least one of said orifices;

at least six reservoirs each in fluid conducting relationship with at least one of said delivery chambers;

means associated with each orifice for propelling fluid through the associated orifice from the delivery chamber that is in fluid conducting relationship with the orifice; and a vent for commonly venting the at least six reservoirs;

wherein each of the reservoirs is in fluid conducting relationship with a plurality of delivery chambers.

27. The apparatus of claim 26 wherein the combined capacity of each said reservoir and delivery chamber in fluid conducting relationship therewith is less than 100 microliters.

28. The apparatus of claim 27, comprising at least sixteen said reservoirs.

29. The apparatus of claim 26, further comprising means for contacting at least one of said orifices with a fluid outside said delivery chamber whereby said fluid will flow from outside the orifice, through the orifice and into the delivery chamber.

30. The apparatus of claim 26, further comprising means operatively connected with said vent for commonly changing the pressure within said at least six reservoirs;

and wherein said pressure changing means comprises means for reducing pressure within said at least six reservoirs.

31. The apparatus of claim 30, further comprising means for contacting at least one of said orifices with a fluid outside said delivery chamber, whereby operating said pressure reducing means results in drawing the fluid through said orifice into said delivery chamber.

32. A method for delivering a plurality of different biological materials onto discrete locations on a receiving surface, the method comprising:

loading a fluid medium containing one of said different biological materials through the orifice and into one of said delivery chambers of the apparatus of claim 30, each said means for propelling when activated propelling a quantity of said fluid medium along a delivery path away from said orifice member;

positioning the apparatus of claim 30 in relation to the receiving surface whereby said orifice member is proximate the receiving surface and the delivery path for said fluid medium intersects said receiving surface at a locus of intersection;

moving the apparatus of claim 30 in relation to the receiving surface whereby a locus of intersection moves on said receiving surface;

activating the means for propelling associated with said orifice when the locus of intersection is at a first location on said surface onto which delivery of said fluid medium is desired; and repeating the moving and activating steps to deliver the plurality of different biological materials onto discrete locations on the surface.

33. Apparatus for delivering a plurality of different biological materials onto discrete locations on a receiving surface, the apparatus comprising:

a plurality of orifices in an orifice member;

a plurality of delivery chambers each in fluid conducting relationship with at least one of said orifices;

at least six reservoirs each in fluid conducting relationship with a plurality of said delivery chambers; and means associated with each orifice for propelling fluid through the associated orifice from the delivery chamber that is in fluid conducting relationship with the orifice;

wherein the combined capacity of each said reservoir and delivery chamber in fluid conducting relationship therewith is less than 100 microliters.

34. The apparatus of claim 33 wherein the combined capacity of each said reservoir and the delivery chambers in fluid conducting relationship therewith is less than 10 microliters.

35. The apparatus of claim 33, further comprising:

a vent for commonly venting the at least six reservoirs;

means operatively connected with said vent for commonly changing the pressure within said at least six reservoirs.

36. The apparatus of claim 35, comprising at least sixteen said reservoirs.

37. The apparatus of claim 35 wherein said pressure changing means comprises means for reducing pressure within said at least six reservoirs.

38. The apparatus of claim 37, further comprising means for contacting at least one of said orifices with a fluid outside said delivery chamber, whereby operating said pressure reducing means results in drawing the fluid through said orifice into said delivery chamber.

39. The apparatus of claim 33, further comprising means for contacting at least one of said orifices with a fluid outside said delivery chamber whereby said fluid will flow from outside the orifice, through the orifice and into the delivery chamber.

40. A method for delivering a plurality of different biological materials onto discrete locations on a receiving surface, using an apparatus having:

a plurality of orifices in an orifice member;

a plurality of delivery chambers each in fluid conducting relationship with at least one of said orifices;

a plurality of reservoirs each in fluid conducting relationship with a plurality of said delivery chambers; and means associated with each orifice for propelling fluid through the associated orifice from the delivery chamber that is in fluid conducting relationship with the orifice;

the method comprising:

loading a fluid medium containing one of said different biological materials into one of said delivery chambers of the apparatus by contacting said orifices with a fluid outside said delivery chamber and permitting said fluid outside to flow through said orifices into said delivery chambers, each said means for propelling when activated propelling a quantity of said fluid medium along a delivery path away from said orifice member;

positioning the apparatus in relation to the receiving surface whereby said orifice member is proximate the receiving surface and the delivery path for said fluid medium intersects said receiving surface at a locus of intersection;

moving the apparatus in relation to the receiving surface so that locus of intersection moves on said receiving surface;

activating the means for propelling associated with said orifice when the locus of intersection is at a first location on said surface onto which delivery of said fluid medium is desired; and repeating the moving and activating steps to deliver the plurality of different biological materials onto discrete locations on the surface.

41. The method of claim 40 wherein said plurality of different biological materials comprises a plurality of nucleic acids.

42. A method according to claim 40 wherein the orifice member is a planar orifice plate having an inner surface and an exit surface, said orifices providing openings through said plate from said inner surface to said outer surface.

43. A head for delivering a plurality of different biological materials onto discrete locations on a receiving surface, the apparatus comprising:

a plurality of orifices in an orifice member;

a plurality of delivery chambers each in fluid conducting relationship with at least one of said orifices;

at least six reservoirs each in fluid conducting relationship with at least one of said delivery chambers;

means associated with each orifice for propelling fluid through the associated orifice from the delivery chamber that is in fluid conducting relationship with the orifice; and a vent for commonly venting the at least six reservoirs, wherein the common vent moves together with the remainder of the head.

44. The head of claim 43, further comprising means for contacting at least one of said orifices with a fluid outside said delivery chamber whereby said fluid will flow from outside the orifice, through the orifice and into the delivery chamber.

45. The head according to claim 43 wherein said means for propelling comprises a source of heat.

46. The head of claim 43 wherein said means for propelling comprises a piezoelectric device.

47. The head of claim 43 wherein the orifice member is a one-piece orifice member.

48. A method for loading a head of claim 47 with a plurality of different biological fluids, comprising contacting said orifices with fluids outside said delivery chamber and permitting said fluids outside to flow through said orifices into said delivery chambers.

49. The head of claim 43 wherein the vent is in a common cover for the at least six reservoirs.

50. The head of claim 49 wherein the combined capacity of each said reservoir and delivery chamber in fluid conducting relationship therewith is less than 100 microliters.

51. The apparatus of claim 50, comprising at least sixteen said reservoirs.

52. The apparatus of claim 49 wherein the combined capacity of each said reservoir and delivery chamber in fluid conducting relationship therewith is less than 10 microliters.

53. The apparatus of claim 52, comprising at least fifty said reservoirs.

54. The apparatus of claim 52, comprising at least one hundred said reservoirs.

55. The apparatus of claim 49 wherein the combined capacity of each said reservoir and delivery chamber in fluid conducting relationship therewith is less than 1 microliter.

56. A method for loading a head or claim 43 with a plurality of different biological fluids, comprising contacting said orifices with a fluid outside said delivery chamber and permitting said fluid outside to flow through said orifices into said delivery chambers.

57. A method of claim 56 additionally comprising reducing the pressure through the common vent to assist the flow of fluid through said orifices.

58. A method according to claim 56 wherein the orifice member is a planar orifice plate having an inner surface and an exit surface, said orifices providing openings through said plate from said inner surface to said outer surface.

* * * * *